United States Patent [19]
Petersen et al.

[11] Patent Number: 5,621,105
[45] Date of Patent: Apr. 15, 1997

[54] PREPARATION OF 7-(AMINOMETHYL-OXA-7-AZA-BICYCLO-[3.3.0]OCT-7-YL) QUINOLONECARBOXYLIC AND 7-(AMINOMETHYL-OXA-7-AZA-BICYCLO-[3.3.0]OCT-7-YL NAPHTHYRIDONECARBOXYLIC ACID DERIVATIVES

[75] Inventors: Uwe Petersen, Leverkusen; Thomas Schenke, Bergisch Gladbach; Klaus Grohe, Odenthal; Klaus-Dieter Bremm, Wuppertal; Rainer Endermann, Wuppertal; Karl G. Metzger, Wuppertal, all of Germany

[73] Assignee: Bayer Aktiengesellschaft, Leverkusen, Germany

[21] Appl. No.: 660,022

[22] Filed: Jun. 6, 1996

Related U.S. Application Data

[62] Division of Ser. No. 320,035, Oct. 7, 1994, which is a division of Ser. No. 124,129, Sep. 20, 1993, Pat. No. 5,395,944.

[30] Foreign Application Priority Data

Sep. 25, 1992 [DE] Germany ............ 42 32 172.7

[51] Int. Cl.$^6$ ............ C07D 471/04; C07D 491/048
[52] U.S. Cl. ............ 546/167; 546/123
[58] Field of Search ............ 546/167, 123

[56] References Cited

U.S. PATENT DOCUMENTS 5,059,597  10/1991  Petersen et al. ............ 514/224.5

FOREIGN PATENT DOCUMENTS 350733  6/1989  European Pat. Off. .
9210191  6/1992  WIPO .

OTHER PUBLICATIONS

Patent Abstracts of Japan, vol. 5, No. 440, Nov. 11, 1991.
Derwent Abstract, Week 9139, p. 9, JO 3188–080–A. 1989.
"Flouro–pyrido:pyridone Derivs. with Oxazino:imidazolyl Substit. are Broad–spectrum Antimicrobial Agents", Banyu Pharm Co., Dec. 16, 1989, JP–325183.

Primary Examiner—David B. Springer
Attorney, Agent, or Firm—Sprung Horn Kramer & Woods

[57] ABSTRACT

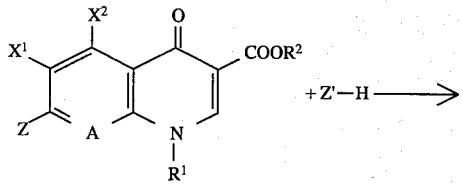

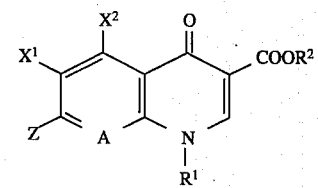

in which
Z represents a residue of the structure

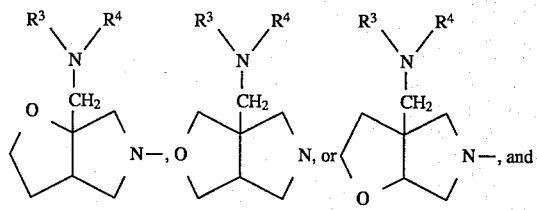

A represents N or C—$R^5$.
The end products are antibacterially active.

3 Claims, No Drawings

PREPARATION OF 7-(AMINOMETHYL-OXA-7-AZA-BICYCLO-[3.3.0]OCT-7-YL) QUINOLONECARBOXYLIC AND 7-(AMINOMETHYL-OXA-7-AZA-BICYCLO-[3.3.0]OCT-7-YL NAPHTHYRIDONECARBOXYLIC ACID DERIVATIVES

This is a division of application Ser. No. 08/320,035, filed on Oct. 7, 1994, now allowed, which is a division of application Ser. No. 08/124,129 filed Sep. 20, 1993, now issued as U.S. Pat. No. 5,395,944.

The invention relates to novel derivatives of quinolonecarboxylic acid and naphthyridonecarboxylic acid which are substituted in the 7 position by a 1- (or 5-)amino-methyl-2- (or 3-)oxa-7-aza-bicyclo[3.3.0]oct-7-yl residue, their salts, processes for their preparation and antibacterial agents containing these compounds.

Quinolonecarboxylic acids which are substituted in the 7 position by a morpholinopyrrolidinyl residue have already become known from European Patent Application 350 733 and Japanese Patent Application 3 188 080.

It has now been found that the compounds of the formula (I)

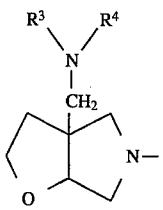

in which
$X^1$ represents halogen or nitro,
$X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl,
$R^1$ represents alkyl having 1 to 4 carbon atoms, alkenyl having 2 to 4 carbon atoms, cycloalkyl having 3 to 6 carbon atoms, which is optionally substituted by halogen, bicyclo[1.1.1]pent-1-yl, 1,1-dimethylpropargyl, 3-oxetanyl, 2-hydroxyethyl, 2-fluoroethyl, methoxy, amino, methylamino, ethylamino, dimethylamino, or phenyl which is optionally substituted by 1 or 2 fluorine atoms,
$R^2$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl,
Z represents a residue of the structure

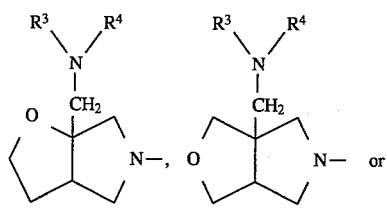

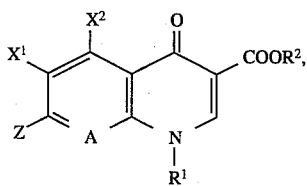

in which
$R^3$ represents hydrogen, methyl or ethyl,
$R^4$ represents hydrogen, acyl having 1 to 3 carbon atoms, alkoxycarbonyl having 1 to 4 carbon atoms in the alkyl moiety, or methyl, and
A represents N or C—$R^5$, in which
$R^5$ represents hydrogen, halogen, methyl, alkenyl having 2 to 3 carbon atoms, alkinyl having 2 to 3 carbon atoms, hydroxyl or methoxy, or, together with $R^1$, can form a bridge of the structure

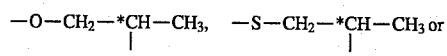

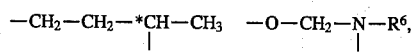

in which $R^6$ denotes hydrogen, methyl or formyl, and their pharmaceutically utilisable hydrates and acid-addition salts, as well as the alkali metal, alkaline earth metal, silver and guanidinium salts of the underlying carboxylic acids, possess a strong antibacterial effect, in particular towards Gram-positive bacteria.

The compounds which are preferred are those of the formula (I)
in which
$X^1$ represents fluorine,
$X^2$ represents hydrogen, amino, methylamino, hydroxyl, methoxy, fluorine, chlorine, bromine or methyl,
$R^1$ represents alkyl having 1 to 3 carbon atoms, vinyl, cycloalkyl having 3 to 4 carbon atoms, 2-(cis- or trans-)fluorocyclopropyl, or phenyl which is optionally substituted by 1 or 2 fluorine atoms,
$R^2$ represents hydrogen, alkyl having 1 to 2 carbon atoms, which is optionally substituted by amino, methylamino or dimethylamino, or (5-methyl-2-oxo-1,3-dioxol-4-yl)-methyl,
Z represents a residue of the structure

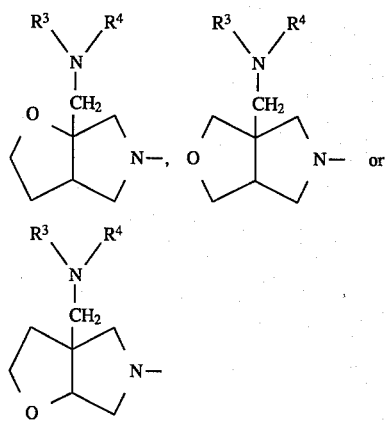

in which
$R^3$ represents hydrogen or methyl, $R^4$ represents hydrogen, acyl having 1 to 2 carbon atoms, alkoxycarbonyl having 1 to 4 carbon atoms in the alkyl moiety, or methyl, and A represents N or C–$R^5$, in which $R^5$ represents hydrogen, fluorine, chlorine, methyl, vinyl, ethinyl or methoxy, or, together with $R^1$, can form a bridge of the structure

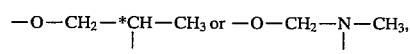

and their pharmaceutically utilisable hydrates and acid-addition salts, as well as the alkali metal, alkaline earth metal, silver and guanidinium salts of the underlying carboxylic acids.

The compounds which are particularly preferred are those of the formula (I)
in which
$X^1$ represents fluorine,
$X^2$ represents hydrogen, amino or fluorine,
$R^1$ represents alkyl having 1 to 2 carbon atoms, cyclopropyl, 2-(cis- or trans-)fluorocyclopropyl, or phenyl which is optionally substituted by 1 or 2 fluorine atoms,
$R^2$ represents hydrogen or alkyl having 1 to 2 carbon atoms,
Z represents a residue of the structure

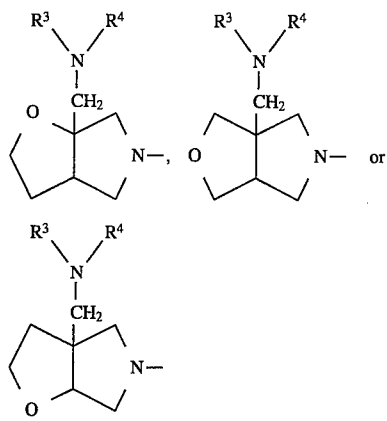

in which $R^3$ represents hydrogen, $R^4$ represents hydrogen or alkoxycarbonyl having 1 to 4 carbon atoms in the alkyl moiety and A represents N or C—$R^5$ in which $R^5$ represents hydrogen, fluorine, chlorine or methoxy, or, together with $R^1$, can form a bridge of the structure

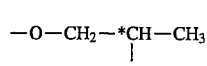

and their pharmaceutically utilisable hydrates and acid-addition salts, as well as the alkali metal, alkaline earth metal, silver and guanidinium salts of the underlying carboxylic acids.

It has furthermore been found that the compounds of the formula (I) are obtained if a compound of the formula (II)

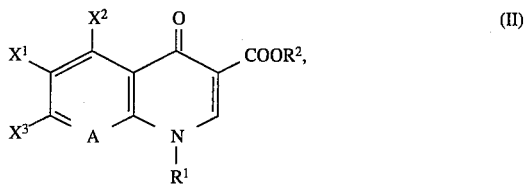

in which
A, $R^1$, $R^2$, $X^1$ and $X^2$ have the abovementioned meaning, and
$X^3$ represents halogen, in particular fluorine or chlorine, is reacted with compounds of the formula (III)
in which
Z' has the meaning given above for Z or represents a residue Z whose amino group can optionally be blocked by a protective group,
optionally in the presence of acid-capturing agents, and protective groups which may optionally be present are eliminated.

If, for example, 1-cyclopropyl-6,7,8-trifluoro-1,4-dihydro-4-oxo-3-quinolinecarboxylic acid and 1-(tert-butyloxy-carbonylaminomethyl)-2-oxa-7-aza-bicyclo[3.3.0]-octane are used as the starting compounds, the course of the reaction can then be represented by the following formula scheme:

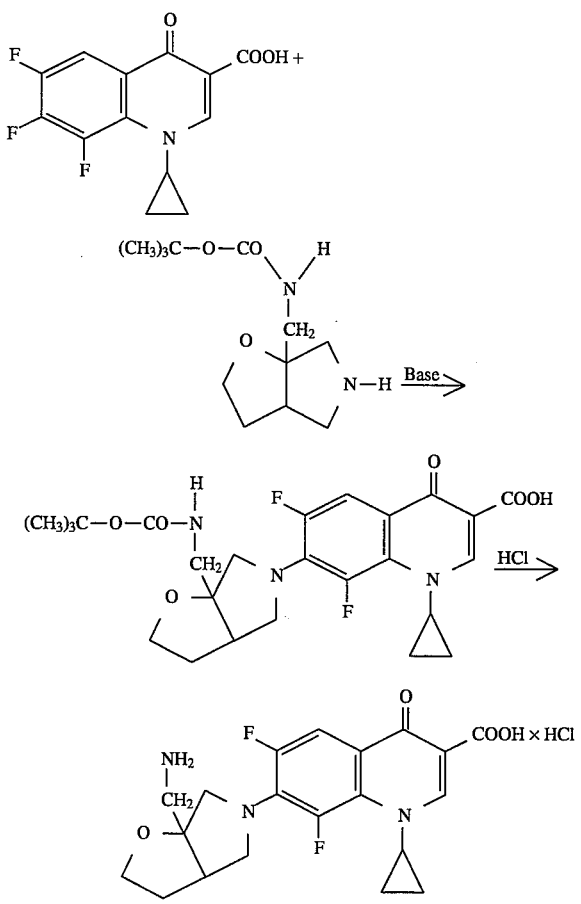

Most of the compounds of the formula (II) used as starting compounds are known or can be prepared by known methods. Examples which may be mentioned are:
7-Chloro-1-cyclopropyl-6-fluoro-1,4-dihydro-4-oxo-3-quinolinecarboxylic acid, 1-Cyclopropyl-6,7-difluoro-1,4-dihydro-4-oxo-3-quinolinecarboxylic acid,
6-Chloro-1-cyclopropyl-7,8-difluoro-1,4-dihydro-4-oxo-3-quinolinecarboxylic acid,
8-Chloro-1-cyclopropyl-6,7-difluoro-1,4-dihydro-4-oxo-3-quinolinecarboxylic acid,
1-Cyclopropyl-6,7,8-trifluoro-1,4-dihydro-4-oxo-3-quinolinecarboxylic acid,
5-Bromo-1-cyclopropyl-6,7,8-trifluoro-1,4-dihydro-4-oxo-3-quinolinecarboxylic acid,
5-Bromo-1-(2,4-difluorophenyl)-6,7,8-trifluoro-1,4-dihydro-4-oxo-3-quinolinecarboxylic acid,
1-Cyclopropyl-6,7-difluoro-1,4-dihydro-8-methyl-4-oxo-3-quinolinecarboxylic acid,
6,7-Difluoro-1-ethyl-1,4-dihydro-4-oxo-3-quinolinecarboxylic acid,
7-Chloro-6-fluoro-1-ethyl-1,4-dihydro-4-oxo-3-quinolinecarboxylic acid,
7-Chloro-6-fluoro-1,4-dihydro-1-(2-hydroxyethyl)-4-oxo-3-quinolinecarboxylic acid,
6,7-Difluoro-1-(2-fluoroethyl)-1,4-dihydro-4-oxo-3-quinolinecarboxylic acid,
7-Chloro-6-fluoro-1,4-dihydro-1-methoxy-4-oxo-3-quinolinecarboxylic acid,
7-Chloro-6-fluoro-1,4-dihydro-1-methylamino-4-oxo-3-quinolinecarboxylic acid,
6,7-Difluoro-1,4-dihydro-4-oxo-1-phenyl-3-quinolinecarboxylic acid,
7-Chloro-1-cyclopropyl-6-fluoro-1,4-dihydro-4-oxo-1,8-naphthyridine-3-carboxylic acid,
Ethyl 7-chloro-1-cyclopropyl-6-fluoro-1,4-dihydro-4-oxo-1,8-naphthyridine-3-carboxylate,
Ethyl 1-cyclopropyl-6,7,8-trifluoro-1,4-dihydro-4-oxo-3-quinolinecarboxylate,
9,10-Difluoro-2,3-dihydro-3-methyl-7-oxo-7H-pyrido-[1,2,3-de][1,4]benzoxazine-6-carboxylic acid,
8,9-Difluoro-6,7-dihydro-5-methyl-1-oxo-1H,5H-benzo[i,j]-quinolizine-2-carboxylic acid,
7-Chloro-6-fluoro-1-phenyl-1,4-dihydro-4-oxo-1,8-naphthyridine-3-carboxylic acid,
Ethyl 7-chloro-6-fluoro-1-(4-fluorophenyl)-1,4-dihydro-4-oxo-1,8-naphthyridine-3-carboxylate,
6,7,8-Trifluoro-1,4-dihydro-1-methylamino-4-oxo-3-quinolinecarboxylic acid,
1-Amino-6,7,8-trifluoro-1,4-dihydro-4-oxo-3-quinolinecarboxylic acid,
6,7,8-Trifluoro-1,4-dihydro-1-dimethylamino-4-oxo-3-quinolinecarboxylic acid,
6,7-Difluoro-1-(4-fluorophenyl)-1,4-dihydro-8-methyl-4-oxo-3-quinolinecarboxylic acid,
7-Chloro-6-fluoro-1-(4-fluorophenyl)-1,4-dihydro-4-oxo-3-quinolinecarboxylic acid,
7-Chloro-6-fluoro-1-(2,4-difluorophenyl)-1,4-dihydro-4-oxo-3-quinolinecarboxylic acid,
6,7,8-Trifluoro-1-(4-fluorophenyl)-1,4-dihydro-4-oxo-3-quinolinecarboxylic acid,
1-Cyclopropyl-6,7-difluoro-1,4-dihydro-5-methyl-4-oxo-3-quinolinecarboxylic acid,
7-Chloro-1-cyclopropyl-6-fluoro-1,4-dihydro-5-methyl-4-oxo-1,8-naphthyridine-3-carboxylic acid,
7-Chloro-6-fluoro-1-(2,4-difluorophenyl)-1,4-dihydro-5-methyl-4-oxo-1,8-naphthyridine-3-carboxylic acid,
6,7-Difluoro-1,4-dihydro-1-(3-oxetanyl)-4-oxo-3-quinolinecarboxylic acid,
6,7,8-Trifluoro-1,4-dihydro-1-(3-oxetanyl)-4-oxo-3-quinolinecarboxylic acid,
1-(Bicyclo[1.1.1]pent-1-yl)-6,7,8-trifluoro-1,4-dihydro-4-oxo-3-quinolinecarboxylic acid,
7-Chloro-1-(1,1-dimethylpropargyl)-6-fluoro-1,4-dihydro-4-oxo-1,8-naphthyridine-3-carboxylic acid,
6,7,8-Trifluoro-1-(2,4-difluorophenyl)-1,4-dihydro-4-oxo-3-quinolinecarboxylic acid,
6,7,8-Trifluoro-1,4-dihydro-4-oxo-1-phenyl-3-quinolinecarboxylic acid,
7-Chloro-1-ethyl-6-fluoro-1,4-dihydro-4-oxo-1,8-naphthyridine-3-carboxylic acid,
6,7-Difluoro-1,4-dihydro-4-oxo-1-vinyl-3-quinolinecarboxylic acid,
1-Cyclopropyl-5,6,7,8-tetrafluoro-1,4-dihydro-4-oxo-3-quinolinecarboxylic acid,
5-Amino-1-cyclopropyl-6,7,8-trifluoro-1,4-dihydro-4-oxo-3-quinolinecarboxylic acid,
1-Cyclopropyl-6,7,8-trifluoro-1,4-dihydro-5-hydroxy-4-oxo-3-quinolinecarboxylic acid,
1-Cyclopropyl-6,7-difluoro-1,4-dihydro-8-methoxy-4-oxo-3-quinolinecarboxylic acid,
7-Chloro-1-(2,4-difluorophenyl)-6-fluoro-1,4-dihydro-4-oxo-1,8-naphthyridine-3-carboxylic acid,
Ethyl 7-chloro-1-(2,4-difluorophenyl)-6-fluoro-1,4-dihydro-4-oxo-1,8-naphthyridine-3-carboxylate,
1-Cyclopropyl-6,7-difluoro-1,4-dihydro-4-oxo-8-vinyl-3-quinolinecarboxylic acid,
1-Cyclopropyl-8-ethinyl-6,7-difluoro-1,4-dihydro-4-oxo-3-quinolinecarboxylic acid,
6,7,8-Trifluoro-1-(cis- and trans-2-fluorocyclopropyl)-1,4-dihydro-4-oxo-3-quinolinecarboxylic acid,
8-Chloro-6,7-difluoro-1-(cis- and trans-2-fluorocyclopropyl)-1,4-dihydro-4-oxo-3-quinolinecarboxylic acid,
7-Chloro-6-fluoro-1-(cis- and trans-2-fluorocyclopropyl)1,4-dihydro-4-oxo-1,8-naphthyridine-3-carboxylic acid,
6,7-Difluoro-1-(cis- and trans-2-fluorocyclopropyl)-1,4-dihydro-4-oxo-3-quinolinecarboxylic acid.

The bicyclic amines of the formula (III) which are required as starting compounds are novel. They may be prepared by the following processes.

The examples are by way of illustration, but are in no way intended to be limiting.

2,3- or 2,5-Dihydrofuran (1) which is substituted at the double bond by an electron-attracting group which can be converted into an aminomethyl group is reacted with an azomethine ylide of the structure (2). The resulting cycloaddition product (3) is subsequently reacted to give the aminomethyl derivative (4), from which the protective group $S_2$ is selectively eliminated. By means of derivatising the aminomethyl group in (4), the corresponding substitution products (7) and (9) can be synthesised via (6) and (8), respectively.

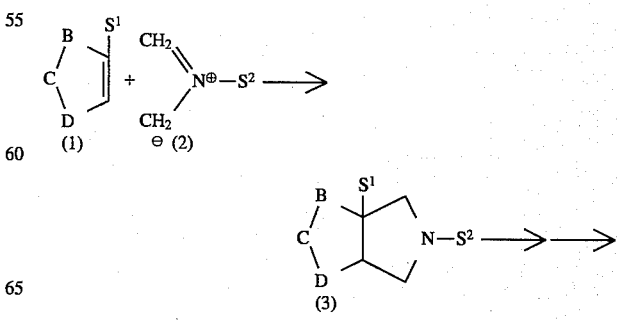

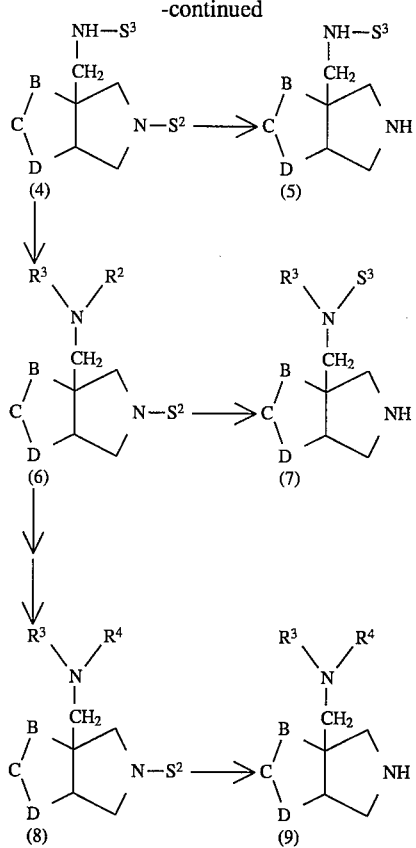

B, C, D: $CH_2$ or oxygen, where one of the groups B, C or D must be oxygen, $S^1$: CN, CO—$NH_2$, CO—$NR^3R^4$, COO-alkyl($C_1$–$C_3$), CO—$CF_3$, CO—$CH_3$, $S^2$: $CH_2$—$C_6H_5$, CO—$C_6H_5$, $S^3$: CO—O-alkyl($C_1$–$C_4$).

If, for example, methyl 2,3-dihydrofuran-4-carboxylate is reacted with N-benzyl-N-methoxymethyl-trimethylsilylmethylamine, the reaction to give 5-tert-butoxycarbonyl-aminomethyl-2-oxa-7-azabicyclo[3.3.0]octane can then be represented by the following reaction scheme:

The following may be mentioned as examples of compounds of the formula (III) which may be employed both as racemates and as enantiomerically pure or diastereomerically pure compounds:

1-Aminomethyl-2-oxa-7-aza-bicyclo[3.3.0]octane,
1-Methylaminomethyl-2-oxa-7-aza-bicyclo[3.3.0]octane,
1-Dimethylaminomethyl-2-oxa-7-aza-bicyclo[3.3.0]octane,
1-Ethylaminomethyl-2-oxa-7-aza-bicyclo[3.3.0]octane,
1-Formylaminomethyl-2-oxa-7-aza-bicyclo[3.3.0]octane,
1-Acetylaminomethyl-2-oxa-7-aza-bicyclo[3.3.0]octane,
1-Methoxycarbonylaminomethyl-2-oxa-7-aza-bicyclo[3.3.0]octane,
1-Ethoxycarbonylaminomethyl-2-oxa-7-aza-bicyclo[3.3.0]octane,
1-tert-Butoxycarbonylaminomethyl-2-oxa-7-aza-bicyclo3.3.0]octane,
1-Aminomethyl-3-oxa-7-aza-bicyclo[3.3.0]octane,
1-Methylaminomethyl-3-oxa-7-aza-bicyclo[3.3.0]octane,
1-Dimethylaminomethyl-3-oxa-7-aza-bicyclo[3.3.0]octane,
1-Ethylaminomethyl-3-oxa-7-aza-bicyclo[3.3.0]octane,
1-Formylaminomethyl-3-oxa-7-aza-bicyclo[3.3.0]octane,
1-Acetylaminomethyl-3-oxa-7-aza-bicyclo[3.3.0]octane,
1-Methoxycarbonylaminomethyl-3-oxa-7-aza-bicyclo[3.3.0]octane,
1-Ethoxycarbonylaminomethyl-3-oxa-7-aza-bicyclo[3.3.0]octane,
1-tert-Butoxycarbonylaminomethyl-3-oxa-7-aza-bicyclo[3.3.0]octane,
5-Aminomethyl-2-oxa-7-aza-bicyclo[3.3.0]octane,
5-Methylaminomethyl-2-oxa-7-aza-bicyclo[3.3.0]octane,
5-Dimethylaminomethyl-2-oxa-7-aza-bicyclo[3.3.0]octane,
5-Ethylaminomethyl-2-oxa-7-aza-bicyclo[3.3.0]octane,
5-Formylaminomethyl-2-oxa-7-aza-bicyclo[3.3.0]octane,
5-Acetylaminomethyl-2-oxa-7-aza-bicyclo[3.3.0]octane,
5-Acetylaminomethyl-2-oxa-7-aza-bicyclo[3.3.0]octane,
5-Methoxycarbonylaminomethyl-2-oxa-7-aza-bicyclo[3.3.0]octane,
5-Ethoxycarbonylaminomethyl-2-oxa-7-aza-bicyclo[3.3.0]octane,
5-tert-Butoxycarbonylaminomethyl-2-oxa-7-aza-bicyclo[3.3.0]octane.

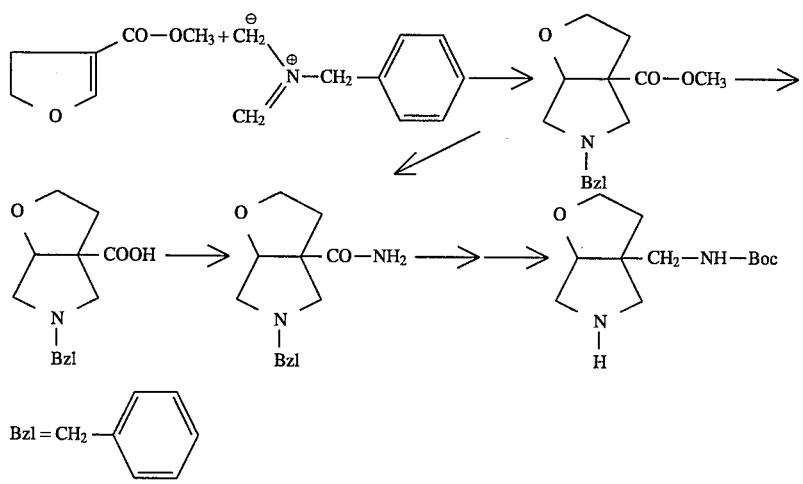

The reaction of (II) with (III), in which the compounds (III) can also be employed in the form of their salts, such as, for example, the hydrochlorides, is preferably undertaken in a diluent, such as dimethyl sulphoxide, N,N-dimethylformamide, N-methylpyrrolidone, hexamethylphosphoric triamide, sulfolane, acetonitrile or water, an alcohol, such as methanol, ethanol, n-propanol, isopropanol or glycol monomethyl ether, or pyridine. Mixtures of these diluents may likewise be used.

All customary inorganic and organic acid-binding agents may be used as acid binders. These preferably include the alkali metal hydroxides, alkali metal carbonates, organic amines and amidines. Those which may be mentioned individually as being particularly suitable are: triethylamine, 1,4-diazabicyclo[2.2.2]octane (DABCO), 1,8-diazabicyclo[5.4.0]undec-7-ene (DBU) or excess amine (III).

The reaction temperatures may be varied over a relatively wide range. In general, temperatures of between about 20° and 200° C., preferably of between 80° and 180° C., are employed.

While the reaction can be carried out under atmospheric pressure, it can also be carried out under elevated pressure. In general, pressures of between about 1 and 100 bar, preferably of between 1 and 10 bar, are employed.

In carrying out the process according to the invention, 1 to 151mol, preferably 1 to 6 mol, of the compound (III) are employed per 1 mol of the compound (II).

During the reaction, free amino groups can be protected by a suitable amino-protective group, e.g. by the tertbutoxycarbonyl radical or as an azomethine group, and, after completion of the reaction, be liberated once more by treatment with a suitable acid, such as hydrochloric acid or trifluoroacetic acid.

To prepare the esters according to the invention, the underlying carboxylic acid is preferably reacted in excess alcohol in the presence of strong acids, such as sulphuric acid, anhydrous hydrogen chloride, methanesulphonic acid, p-toluenesulphonic acid or acid ion exchangers, and at temperatures of about 20° to 200° C., preferably of about 60° to 120° C. The resulting reaction water can also be removed by means of azeotropic distillation using chloroform, tetrachloromethane, benzene or toluene.

The preparation of esters is also advantageously achieved by heating the underlying acid with a dimethylformamide dialkyl acetal in a solvent such as dimethylformamide.

The 5-methyl-2-oxo-1,3-dioxol-4-yl-methyl esters, which are used as prodrugs, are obtained by reacting an alkali metal salt of the underlying carboxylic acid, which can optionally be protected on the N atom by a protective group such as the tert-butoxycarbonyl radical, with 4-bromomethyl- or 4-chloromethyl-5-methyl-1,3-dioxol-2-one in a solvent such as dimethylformamide, dimethylacetamide, N-methylpyrrolidone, dimethyl sulphoxide or tetramethylurea at temperatures of about 0° to 100° C., preferably of 0° to 50° C.

The acid-addition salts of the compounds according to the invention are prepared in a customary manner, for example by dissolving the betaine in excess aqueous acid and precipitating the salt with an organic solvent which is miscible with water, such as methanol, ethanol, acetone or acetonitrile. The equivalent quantities of betaine and acid can also be heated in water or an alcohol, such as glycol monomethyl ether, and the mixture subsequently evaporated to dryness, or the precipitated salt filtered off with suction. Pharmaceutically utilisable salts are understood to mean, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in a sub-equivalent quantity of alkali metal hydroxide or alkaline earth metal hydroxide, filtering off undissolved betaine and evaporating the filtrate to dryness. Sodium, potassium or calcium salts are pharmaceutically suitable. The corresponding silver salts are obtained by reacting an alkali metal or alkaline earth metal salt with a suitable silver salt such as silver nitrate.

Besides the active compounds named in the examples, the active compounds listed in the following table, which compounds can be present as racemates or as enantiomerically pure or diastereomerically pure compounds, can also be prepared:

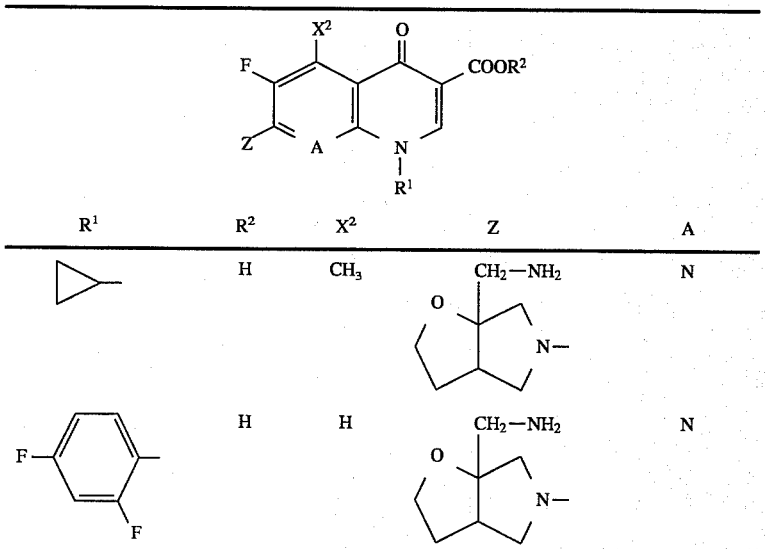

-continued
| R¹ | R² | X² | Z | A |
|---|---|---|---|---|
| 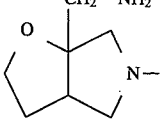 | H | Cl |  CH₂—NH₂ | C—Cl |
| 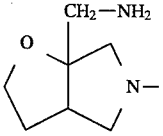 | H | NH₂ |  CH₂—NH₂ | C—OCH₃ |
| 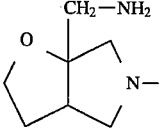 | H | H |  CH₂—NH₂ | C—CH₃ |
| 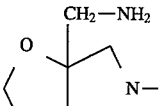 | H | CH₃ |  CH₂—NH₂ | CH |
| 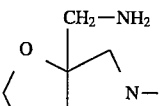 | H | CH₃ |  CH₂—NH₂ | CF |
| 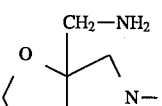 | H | H |  CH₂—NH₂ | C—Br |
| 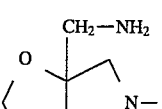 | H | Br | 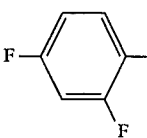 CH₂—NH₂ | CF |
| 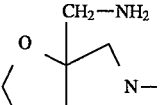 | H | Br | CH₂—NH₂ | CF |
| 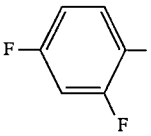 | H | F | 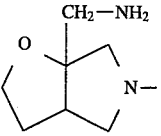 CH₂—NH₂ | CF |

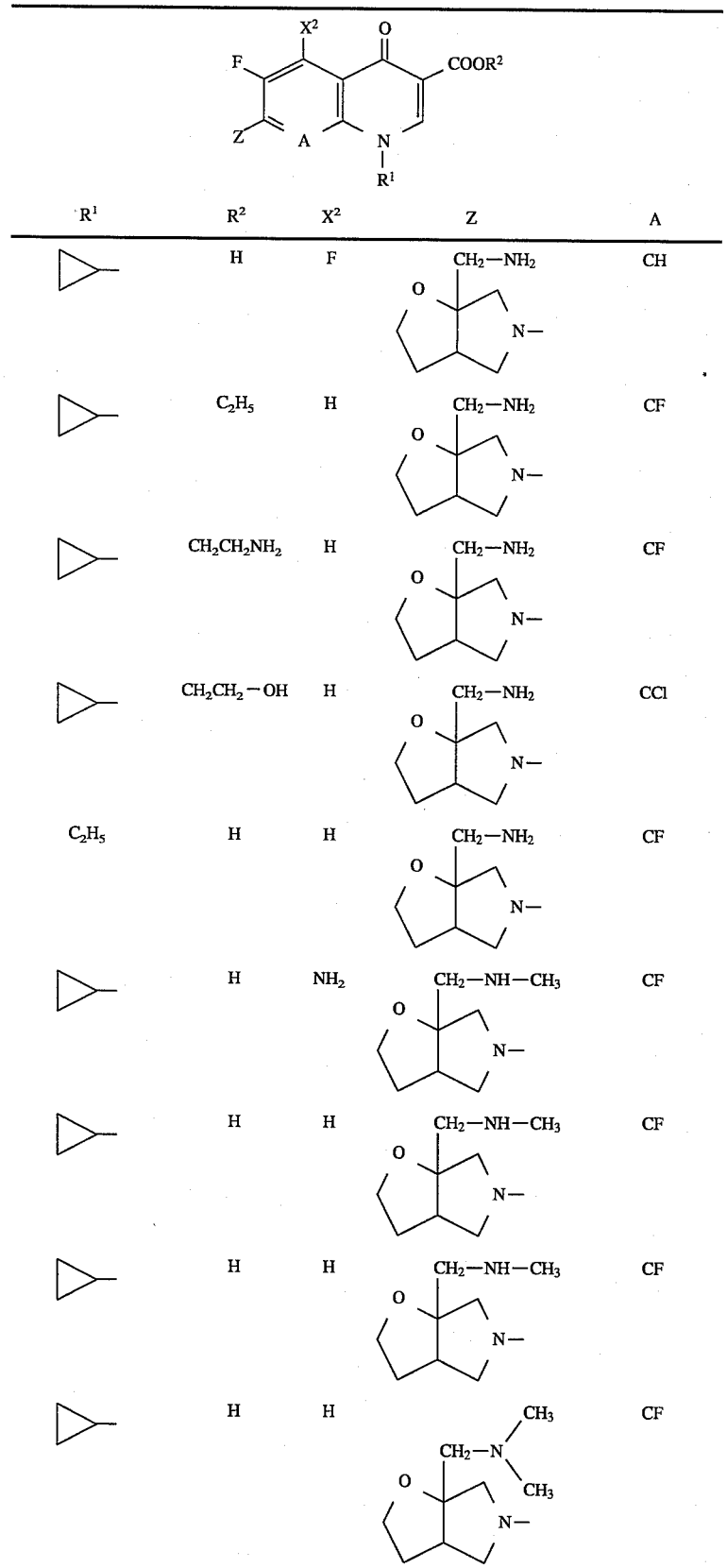

-continued
| R¹ | R² | X² | Z | A |
|---|---|---|---|---|
| 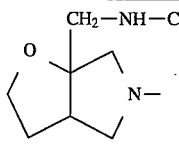 | H | H |  | CF |
| 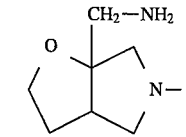 | H | H |  | CF |
| 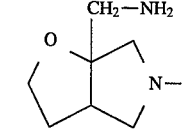 | H | NH₂ |  | CF |
| 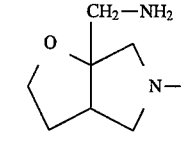 | H | H |  | CCl |
| 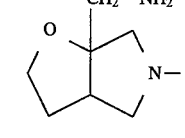 | H | H |  | N |
| 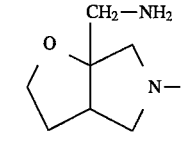 | H | H |  | C—CH=CH₂ |
| 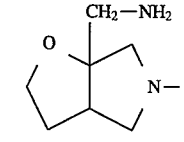 | H | H |  | C—CH≡CH |
| 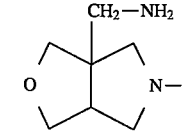 | H | NH₂ |  | CF |
| 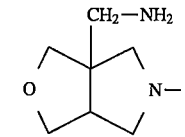 | H | H | (structure) | N |

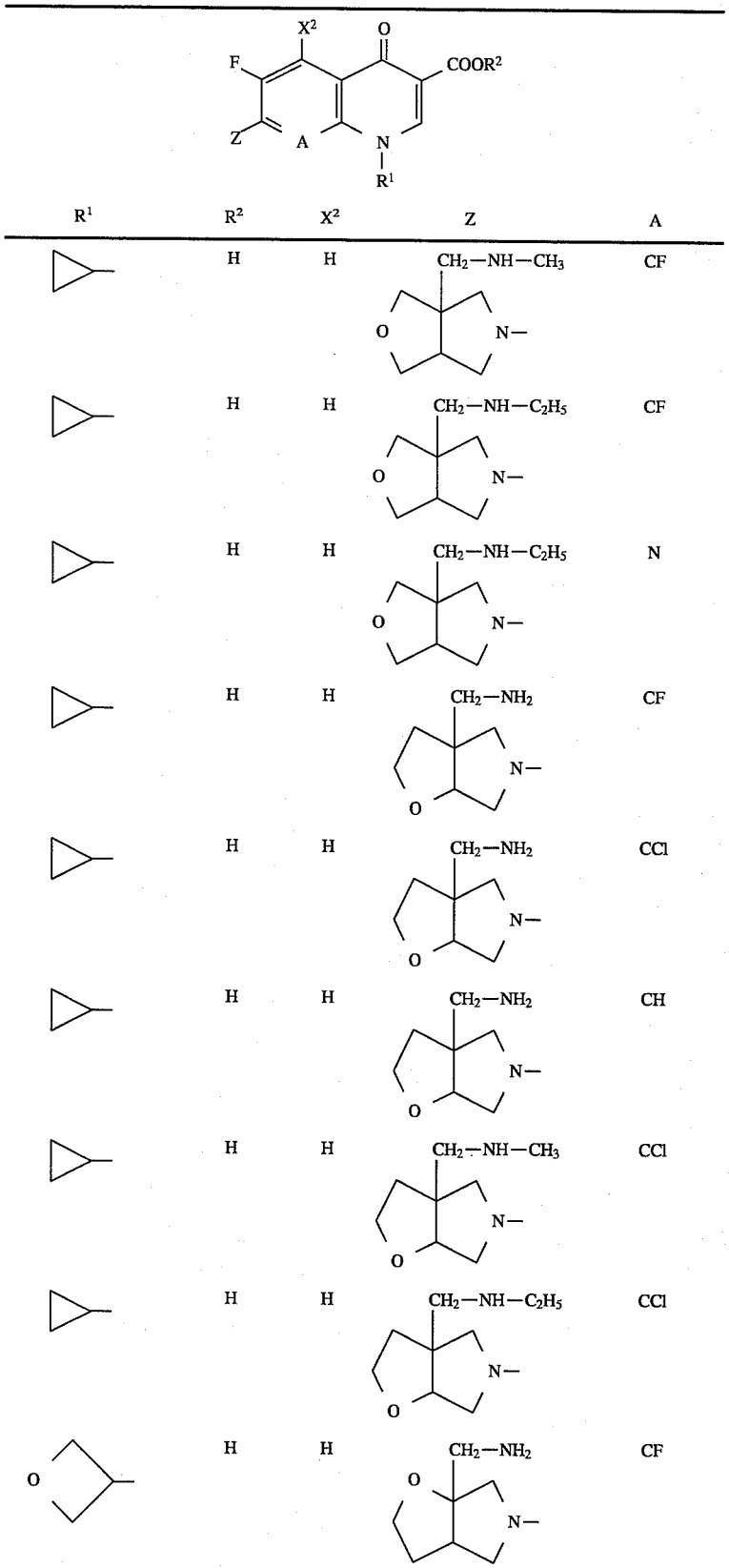

-continued

[Structure: quinolone core with F, $X^2$, O, $COOR^2$ substituents, Z, A positions, N-$R^1$]

| $R^1$ | $R^2$ | $X^2$ | Z | A |
|---|---|---|---|---|
| $F-CH_2CH_2-$ | H | H | $CH_2-NH_2$ on bicyclic O/N ring | CF |
| $CH_3-NH-$ | H | H | $CH_2-NH_2$ on bicyclic O/N ring | CF |
| $F-$phenyl | H | H | $CH_2-NH_2$ on bicyclic O/N ring | CF |
| bicyclobutyl | H | H | $CH_2-NH_2$ on bicyclic O/N ring | CF |

The compounds according to the invention have a strong antibiotic effect and exhibit, while being of low toxicity, a broad antibacterial spectrum against Gram-positive and Gram-negative organisms, in particular against enterobacteria; especially also against those which are resistant to a variety of antibiotics, such as, for example, penicillins, cephalosporins, aminoglycosides, sulfonamides and tetracyclines.

These valuable properties permit their use as chemotherapeutic active compounds in medicine and as compounds for preserving inorganic and organic materials, in particular organic materials of all kinds, e.g. polymers, lubricants, paints, fibres, leather, paper and wood, and foodstuffs and water.

The compounds according to the invention are effective against a very broad spectrum of microorganisms. Using them, Gram-negative and Gram-positive bacteria and bacteria-like microorganisms can be controlled and the diseases caused by these pathogens can be prevented, ameliorated and/or cured.

The compounds according to the invention are distinguished by an increased effect on resistant organisms. In the case of bacteria which exhibit no detectable growth, the compounds have a stronger bactericidal effect than previously known substances. This refers not only to the quantity to be employed but also to the speed of killing. It was possible to observe results of this nature with Gram-positive and Gram-negative bacteria, in particular with *Staphylococcus aureus, Pseudomonas aeruginosa, Enterococcus faecalis* and *Escherichia coli*.

The compounds according to the invention also exhibit surprising increases in effect against bacteria which are categorised as being less sensitive towards comparable substances, in particular resistant *Staphylococcus aureus, Escherichia coli, Pseudomonas aeruginosa* and *Enterococcus faecalis*.

The compounds according to the invention are particularly effective against bacteria and bacteria-like microorganisms. They are therefore particularly suitable for the prophylaxis and chemotherapy of local and systemic infections in human and veterinary medicine which are caused by these pathogens.

In addition, the compounds are suitable for controlling protozoiases and helminthiases.

The compounds according to the invention may be used in various pharmaceutical preparations. Those pharmaceutical preparations which may be mentioned as being preferred are tablets, coated tablets, capsules, pills, granules, suppositories, solutions, suspensions and emulsions, pastes, ointments, gels, creams, lotions, powders and sprays.

The compounds according to the invention can also be combined, via covalent bonds, with β-lactam derivatives, such as, for example, cephalosporins or penicillins, to give dual-action derivatives.

The minimum inhibitory concentrations (MIC) were determined by means of serial dilution methods on Iso-Sensitest agar (Oxoid). For each substance to be tested, a series of agar plates was prepared which contained concentrations of the active compound which in each case decreased by a doubling dilution. The agar plates were inoculated with a Multipoint inoculator (Denley). For the inoculation, overnight cultures of the pathogens were used which had previously been diluted so that each inoculation spot contained about $10^4$ colony-forming particles. The inoculated agar plates were incubated at 37° C. and the organism growth was recorded after about 20 hours. The MIC value (μg/ml) indicates the lowest concentration of active compound at which no growth was detected with the naked eye.

In the table below, the MIC values of some of the compounds according to the invention are listed in comparison with 1-cyclopropyl-6,8-difluoro-1,4-dihydro-7-(cis-2-oxa-5,8-diazabicyclo[4.3.0]non-8-yl)-4-oxo-3-quinolinecarboxylic acid hydrochloride (reference example A) and 8-chloro-1-cyclopropyl-6-fluoro-1,4-dihydro-7-(cis-2-oxa-5,8-diazabicyclo[4.3.0]non-8-yl)-4-oxo-3-quinolinecarboxylic acid hydrochloride (reference example B).

|  |  | MIC values | | | |
| --- | --- | --- | --- | --- | --- |
| Organisms | | Example 1B | Example 2B | Reference example A | Reference example B |
| Escherichia coli | 455/7 | 2 | 1 | 4 | 2 |
| Klebsiella pneumoniae | 8085 | 0.06 | 0.03 | 0.06 | 0.06 |
| Enterobacter cloacae | 2427 | 0.06 | 0.06 | 0.125 | 0.25 |
| Enterobacter aerog. | ICB 5240 | 8 | 8 | 32 | 16 |
| Morganella morganii | 932 | 0.03 | 0.03 | 0.125 | 0.06 |
| Providencia sp. | 12012 | 0.06 | 0.03 | 0.125 | 0.06 |
| Micrococcus luteus | 9341 | 0.25 | 0.125 | 0.5 | 0.25 |
| Staphylococcus aureus | ICB 25701 | 1 | 0.25 | 2 | 0.5 |
|  | 1756 | ≦0.015 | 0.0039 | 0.06 | 0.015 |
|  | 133 | 0.06 | 0.015 | 0.06 | 0.03 |
| Enterococcus faecalis | 27101 | 0.06 | 0.03 | 0.25 | 0.125 |
|  | 9790 | 0.125 | 0.06 | 0.25 | 0.125 |
| Pseudomonas aeruginosa | ICB 308029 | 16 | 32 | 64 | 64 |

Preparation of the Intermediates

EXAMPLE A a) 7-Benzyl-1-cyano-2-oxa-7-azabicyclo[3.3.0]octane 14.4 g (0.15 mol) of 4,5-dihydrofuran-2-carbonitrile are introduced in 300 ml of absolute methylene chloride, 1.8 g of triethylamine and 1.8 g of trifluoroacetic acid are added, and the mixture is warmed to 40° C. 42.6 g (0.15 mol) of N-benzyl-N-methoxymethyl-N-trimethylsilylmethylamine are added dropwise to this mixture which is then stirred at 40° C. for 15 hours. It is then washed with 50 ml of saturated sodium hydrogen carbonate solution, dried over MgSO₄, concentrated and distilled twice. Yield: 9.3 g (22.5% of theory) Boiling point: 120°–125° C./0.06 mbar The product is 83% pure by gas chromatography.

b) 1-Aminomethyl-7-benzyl-2-oxa-7-aza-bicyclo[3.3.0]octane 10.2 g (40 mmol, 90% pure) of 7-benzyl-1-cyano-2-oxa-7-aza-bicyclo[3.3.0]octane are added dropwise to 2 g of lithium aluminium hydride in 100 ml of absolute tetrahydrofuran and the mixture is subsequently stirred under reflux for 15 hours. 2 ml each of water, 15% strength potassium hydroxide solution, and again water, are added dropwise, the inorganic salts are filtered off with suction, and the filtrate is concentrated and distilled. Yield: 7.7 g (83% of theory).

c) 7-Benzyl-1-tert-butoxycarbonylaminomethyl-2-oxa-7-aza-bicyclo[3.3.0]octane 2 g of NaOH in 45 ml of water are added to 10.4 g (44.7 mmol) of 1-aminomethyl-7-benzyl-2-oxa-7-azabicyclo [3.3.0]octane in 56 ml of tert-butanol, and 10.2 g (47 mmol) of di-tert-butyl pyrodicarbonate are then added dropwise. The mixture is stirred at room temperature for 15 hours, and then extraction with chloroform, drying over potassium carbonate, concentration and distillation are carried out. Yield: 12.2 g (82% of theory) Boiling point: 170° C./0.15 mbar The product is 94% pure by gas chromatography.

d) 1-tert-Butoxycarbonylaminomethyl-2-oxa-7-azabicyclo[3.3.0]octane 12.2 g (34.5 mmol) of 7-benzyl-1-tert-butoxycarbonylaminomethyl-2-oxa-7-aza-bicyclo[3.3.0]octane are hydrogenated in 200 ml of ethanol on 7 g of palladium-active charcoal (10% Pd) at 100° C. and 100 bar. The catalyst is filtered off with suction and the filtrate is concentrated and distilled. Yield: 5.7 g (68% of theory) Boiling point: 120°–130° C./0.01 mbar.

EXAMPLE B

1-Aminomethyl-3-oxa-7-azabicyclo[3.3.0]octane a) 3-Cyano-2,5-dihydrofuran 17.2 g (0.2 mol) of 3-oxotetrahydrofuran and 1 g of zinc iodide are initially introduced in 100 ml of benzene, and 24 g (0.24 mol) of trimethylsilyl cyanide are added dropwise. The mixture is stirred at room temperature overnight, 300 ml of pyridine are added, and then 92 g (0.6 mol) of phosphorus oxychloride are added dropwise. Subsequently, the mixture is heated under reflux for 20 hours. It is then poured onto ice and extracted with diethyl ether. The ether solutions are washed with sodium chloride solution, dried over magnesium sulphate, concentrated and distilled. Yield: 10 g (24% of theory) Boiling point: 80° C./20 mbar By GC-MS, the product contains 45% of 3-cyano-2,5-dihydrofuran, 17% of 3-cyano-4,5-dihydrofuran and 37% of 3-chloro-3-cyano-tetrahydrofuran.

b) 7-Benzyl-1-cyano-3-oxa-7-azabicyclo[3.3.0]octane

A solution of 5.2 g (24.6 mmol, 46% strength) of 3-cyano-2,5-dihydrofuran in 50 ml of absolute methylene chloride is mixed with 0.3 g of triethylamine and 0.3 g of trifluoroacetic acid, the mixture is heated under reflux and then 7 g (29.5 mmol) of N-benzyl-N-methoxymethyl-N-(trimethylsilylmethyl)-amine are added dropwise. Subsequently, the mixture is heated under reflux for 2 hours and the solution is washed with saturated sodium hydrogen carbonate solution, dried over magnesium sulphate, concentrated and distilled. Yield: 4.5 g (80% of theory). Boiling point: 140°–145° C./0.03 mbar c) 1-Aminomethyl-7-benzyl-3-oxa-7-azabicyclo[3.3.0]octane 3.7 g (15.9 mmol) of 7-benzyl-1-cyano-3-oxa-7-azabicyclo[3.3.0]octane in 5 ml of absolute tetrahydrofuran are added dropwise to a mixture of 1.5 g of lithium aluminium hydride in 100 ml of absolute tetrahydrofuran and the resulting mixture is heated under reflux for 15 hours. Decomposition is effected with 1.5 ml each of water, 15% strength sodium hydroxide solution, and again water, and the mixture is filtered with suction, and the aluminium salts are extracted by boiling on two occasions with 100 ml of tetrahydrofuran. The tetrahydrofuran solutions are concentrated and the residue is distilled. Yield: 3.2 g (86% of theory) Boiling point: 125°–130° C./0.04 mbar d) 1-Aminomethyl-3-oxa-7-azabicyclo[3.3.0]octane 2.8 g (12.1 mmol) of 1-aminomethyl-7-azabicyclo[3.3.0]octane are dissolved in 50 ml of ethanol and hydrogenated on 0.3 g of palladium-active charcoal at 100° C. and 100 bar. The catalyst is filtered off with suction and the filtrate is concentrated and distilled. Yield: 1.5 g (87% of theory) Boiling point: 70°–72° C./0.03 mbar.

EXAMPLE 1

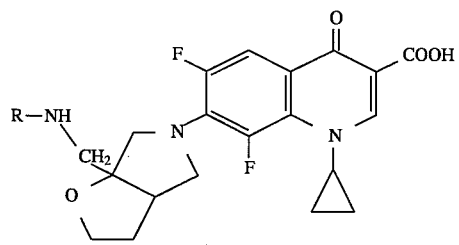

A: R = (CH$_3$)$_3$C—O—CO

B: R = H × HCl

A: A mixture of 1.42 g (5 mmol) of 1-cyclopropyl6,7,8-trifluoro-1,4-dihydro-4-oxo-3-quinolinecarboxylic acid in 15 ml of acetonitrile and 7.5 ml of dimethylformamide is heated under reflux for 1 hour together with 560 mg (5 mmol) of 1,4-diazabicyclo[2.2.2]octane and 1.3 g (5.4 mmol) of 1-tert-butoxycarbonylaminomethyl-2-oxa-7-azabicyclo[3.3.0]octane. The suspension is cooled and the precipitate is filtered off with suction, washed with water and recrystallised from acetonitrile.

Yield: 1.2 g (48.5% of theory) of 7-(1-tert-butoxy-carbonylaminomethyl-2-oxa-7-azabicyclo[3.3.0]oct-7-yl)-1-cyclopropyl-6,8-difluoro-1,4-dihydro-4-oxo-3-quinolinecarboxylic acid, Melting point: 188°–190° C. (with decomposition).

B: 1.1 g (2.2 mmol) of 7-(1-tert-butoxycarbonylaminomethyl-2-oxa-7-azabicyclo[3.3.0]oct-7-yl)-1-cyclopropyl-6,8-difluoro-1,4-dihydro-4-oxo-3-quinolinecarboxylic acid are dissolved in 30 ml of hot half-concentrated hydrochloric acid, and the solution is filtered and concentrated at 70° C. and 12 mbar. 40 ml of ethanol are added to the residue, the mixture is cooled in ice, and the precipitated salt is filtered off with suction, washed with ethanol and dried at 100° C. under high vacuum.

Yield: 690 mg (72% of theory) of 7-(1-aminomethyl-2-oxa-7-aza-bicyclo[3.3.0]oct-7-yl) -1-cyclopropyl-6,8-difluoro-1,4-dihydro-4-oxo-3-quinolinecarboxylic acid hydrochloride, Melting point: 187°–204° C. (with decomposition).

EXAMPLE 2

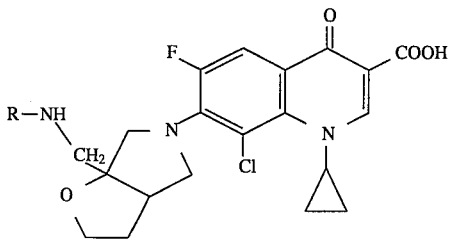

A: R = (CH$_3$)$_3$C—O—CO

B: R = H × CF$_3$COOH

A: In an analogous manner to Example 1A, reaction is effected with 8-chloro-1-cyclopropyl-6,7-difluoro-1,4-dihydro-4-oxo-3-quinolinecarboxylic acid to give 7-(1-tert-butoxycarbonylaminomethyl-2-oxa-7-aza-bicyclo[3.3.0]oct-7-yl)-8-chloro-1-cyclopropyl-6-fluoro-1,4-dihydro-4-oxo-3-quinolinecarboxylic acid (88% of theory) with a melting point of 111°–113° C. (recrystallised from ethanol).

B: 2.2 g ( 4.2 mmol ) of 7-(1-tert-butoxycarbonylaminomethyl-2-oxa-7-aza-bicyclo[3.3.0]oct-7-yl)-8-chloro-1-cyclopropyl-6-fluoro-1,4-dihydro-4-oxo-3-quinolinecarboxylic acid are dissolved in 5 ml of trifluoroacetic acid, and after having stood at room temperature for 12 hours the solution is evaporated, and the remaining yellow oil is treated several times with methylene chloride in an ultrasonic bath until it crystallises. The salt was filtered off with suction, washed with methylene chloride and dried at 100° C. under high vacuum.

Yield: 1.27 g (56% of theory) of 7-(1-aminomethyl-2-oxa-7-aza-bicyclo[3.3.0]oct-7-yl)-8-chloro-1-cyclopropyl-6-fluoro-1,4-dihydro-4-oxo-3-quinolinecarboxylic acid trifluoroacetate, Melting point: 230°–233° C. (with decomposition).

EXAMPLE 3

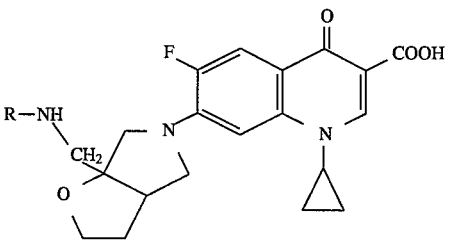

A: R = (CH$_3$)$_3$C—O—CO

B: R = H × HCl

A: In an analogous manner to Example 1A, reaction is effected with 1-cyclopropyl-6,7-difluoro-1,4-dihydro-4-oxo-3-quinolinecarboxylic acid to give 7-(1-tertbutoxycarbonylaminomethyl-2-oxa-7-aza-bicyclo[3.3.0]oct-7-yl)-1-cyclopropyl-6-fluoro-1,4-dihydro-4-oxo-3-quinolinecarboxylic acid (98% of theory) with a melting point of 235°–237° C. (recrystallised from glycol monomethyl ether).

B: In an analogous manner to Example 1B, the product from step A is reacted with half-concentrated hydrochloric acid to give 7-( 1-aminomethyl-2-oxa-7-aza-bicyclo[3.3.0]- oct-7-yl)-1-cyclopropyl-6-fluoro-1,4-dihydro-4-oxo-3-quinolinecarboxylic acid hydrochloride with a melting point of 223°–226° C. (with decomposition).

EXAMPLE 4

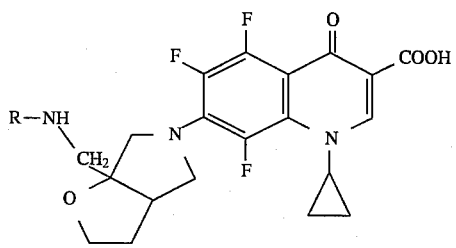

A: R = (CH₃)₃C—O—CO

B: R = H × HCl

A: In an analogous manner to Example 1A, reaction is effected with 1-cyclopropyl-5,6,7,8-tetrafluoro-1,4-dihydro-4-oxo-3-quinolinecarboxylic acid to give 7-(1-tert-butoxycarbonylaminomethyl-2-oxa-7-aza-bicyclo[3.3.0]oct-7-yl)-1-cyclopropyl-5,6,8-trifluoro-1,4-dihydro-4-oxo-3-quinolinecarboxylic acid (95% of theory) with a melting point of 226°–228° C. (with decomposition) (recrystallised from glycol monomethyl ether).

B: In an analogous manner to Example 1B, the product from step A is reacted with half-concentrated hydrochloric acid to give 7-(1-aminomethyl-2-oxa-7-aza-bicyclo[3.3.0]oct-7-yl)-1-cyclopropyl-5,6,8-trifluoro-1,4-dihydro-4-oxo-3-quinolinecarboxylic acid hydrochloride with a melting point of 175°–177° C. (with decomposition).

EXAMPLE 5

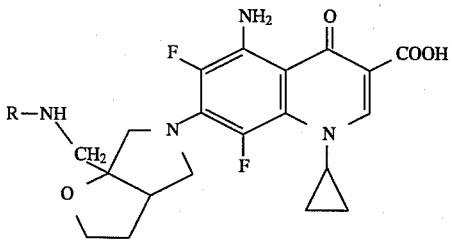

A: R = (CH₃)₃C—O—CO

B: R = H × HCl

A: 1 g (1.9 mmol) of 7-(1-tert-butoxycarbonylaminomethyl-2-oxa-7-aza-bicyclo[3.3.0]oct-7-yl)-1-cyclopropyl-5,6,8-trifluro-1,4-dihydro-4-oxo-3-quinolinecarboxylic acid is dissolved in 30 ml of dimethyl sulphoxide, and a stream of ammonia is passed through the solution at 130°–140° C. for a period of 5 hours. When the starting compound can no longer be detected by thin layer chromatography (silica gel; methylene chloride/methanol/17% aqueous ammonia 150:20:1), the mixture is evaporated under high vacuum, the residue is stirred with 30 ml of water, and the suspension is left to stand overnight. The precipitate which separates out is filtered off with suction, washed with water and dried. The resulting crude product (580 mg) is recrystallised from glycol monomethyl ether.

Yield: 290 mg (29% of theory) of 5-amino-7-(1-tert-butoxycarbonylaminomethyl-2-oxa-7-aza-bicyclo [3.3.0] oct-7-yl)-1-cyclopropyl-6,8-difluoro-1,4-dihydro-4-oxo-3-quinolinecarboxylic acid with a melting point of 181°–183° C. (with decomposition).

B: In an analogous manner to Example 1B, the product from step A is reacted with half-concentrated hydrochloric acid to give 5-amino-7-(1-aminomethyl-2-oxa-7-azabicyclo[3.3.0.]oct-7-yl)-1-cyclopropyl-6,8-difluoro-1,4-dihydro-4-oxo-3-quinolinecarboxylic acid hydrochloride with a melting point of 262°–263° C. (with decomposition).

FAB-MS: m/e 421 [(M+H)⁺], 841 [(2M+H)⁺].

EXAMPLE 6

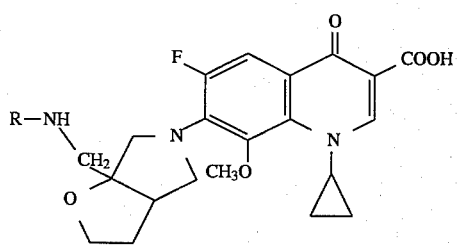

A: R = (CH₃)₃C—O—CO

B: R = H × HCl

A: In an analogous manner to Example 1A, reaction is effected with 1-cyclopropyl-6,7-difluoro-1,4-dihydro-8-methoxy-4-oxo-3-quinolinecarboxylic acid, and the reaction product is purified by chromatography on silica gel using methylene chloride/methanol/17% aqueous ammonia (470:20:1). 7-(1-tert-butoxycarbonylaminomethyl-2-oxa-7-aza-bicyclo[3.3.0]oct-7-yl)-1-cyclopropyl-6,8-difluoro-1,4-dihydro-8-methoxy-4-oxo-3-quinolinecarboxylic acid is obtained in 23% yield. CI-MS: m/e 518 [(M+H)⁺].

B: 15 mg of the product from step A are left to stand at room temperature for 1 day in a mixture consisting of 1 ml of methanol and 3 drops of concentrated hydrochloric acid. Monitoring of the reaction is effected by thin layer chromatography (silica gel, methylene chloride/methanol/17% ammonia 30:8:1). After elimination of the protective group, the solution is concentrated, and the residue is triturated with a little ethanol, filtered off with suction and dried.

Yield: 11.8 mg (90% of theory) of 7-(1-aminomethyl-2-oxa-7-aza-bicyclo[3.3.0]oct-7-yl)-1-cyclopropyl-6,8-difluoro-1,4-dihydro-8-methoxy-4-oxo-3-quinolinecarboxylic acid hydrochloride, CI-MS: m/e 418 [(M+H)⁺]; the methyl ester can additionally be detected at lower intensity as a byproduct: m/e 432.

EXAMPLE 7

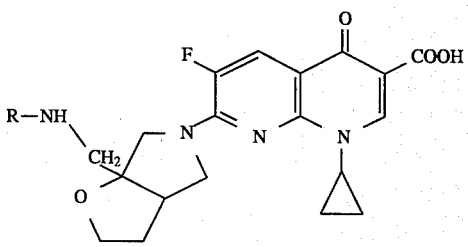

A: R = (CH₃)₃C—O—CO

B: R = H × HCl

A: 130 mg (1.16 mmol) of 1,4-diazabicyclo[2.2.2]octane and 250 mg (1.03 mmol) of 1-tert-butoxycarbonylaminomethyl-2-oxa-7-aza-bicyclo[3.3.0]octane are added to 283 mg (1 mmol) of 6-chloro-1-cyclopropyl-7-fluoro-1,4-dihydro-4-oxo-1,8-naphthyridone- 3-carboxylic acid in 5 ml of acetonitrile, and the mixture is stirred at 50° C. for 2 hours with the exclusion of water. The precipitated product is filtered off with suction, washed with water, dried and purified by chromatography (silica gel; methylene chloride/methanol 95:5).

Yield: 87 mg (18% of theory) of 7-(1-tert-butoxycarbonyl-aminomethyl-2-oxa-7-aza-bicyclo[3.3.0]oct-7-yl)-1-cyclopropyl-6-fluoro-1,4-dihydro-4-oxo-1,8-naphthyridine-3-carboxylic acid, $^1$H-NMR (CDCl$_3$): δ 8.35 s (1H), 8.0 ppm d (1H).

B: 70 mg (0.14 mmol) of the product from step A are dissolved in 1 ml of warm half-concentrated hydrochloric acid, and the solution is filtered and evaporated, and the residue is stirred with a little ethanol. The salt is filtered off with suction, washed with ethanol and dried.

Yield: 45 mg (74% of theory) of 7-(1-aminomethyl-2-oxa-7-aza-bicyclo[3.3.0]oct-7-yl)-2-cyclopropyl-6-fluoro-1,4-dihydro-4-oxo-1,8-naphthyridine-3-carboxylic acid hydrochloride, Melting point: 220°–221° C. (with decomposition).

EXAMPLE 8

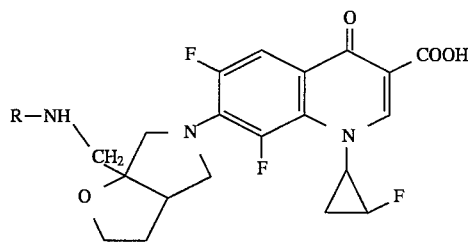

A: R = (CH$_3$)$_3$C—O—CO

B: R = H × HCl

A: In an analogous manner to Example 1A, reaction is effected with 6,7,8-trifluoro-1-(cis-2-fluorocyclopropyl)-1,4-dihydro-4-oxo-3-quinolinecarboxylic acid to give 7-(1-tert-butoxycarbonylaminomethyl-2-oxa-7-aza-bicyclo[3.3.0]oct-7-yl)-6,8-difluoro-1-(cis-2-fluoro-cyclopropyl)-1,4-dihydro-4-oxo-3-quinolinecarboxylic acid (73% of theory) with a melting point of 121°–129° C. (with decomposition).

B: In an analogous manner to Example 1B, the product from step A is reacted with half-concentrated hydrochloric acid to give 7-(1-aminomethyl-2-oxa-7-aza-bicyclo[3.3.0]-oct-7-yl)-6,8-difluoro-1-(cis-2-fluorocyclopropyl)-1,4-dihydro-4-oxo-3-quinolinecarboxylic acid hydrochloride with a melting point of 220°–227° C. (with decomposition).

EXAMPLE 9

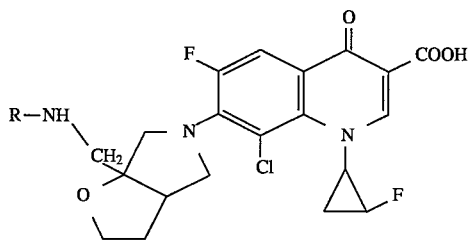

A: R = (CH$_3$)$_3$C—O—CO

B: R = H × HCl

A: In an analogous manner to Example 1A, reaction is effected with 8-chloro-6,7-difluoro-1-(cis-2-fluorocyclopropyl)-1,4-dihydro-4-oxo-3-quinolinecarboxylic acid to give 7-(1-tert-butoxycarbonylaminomethyl-2-oxa-7-aza-bicyclo[3.3.0]oct-7-yl)-8-chloro-6-fluoro-1-(cis-2-fluorocyclopropyl)-1,4-dihydro-4-oxo-3-quinolinecarboxylic acid (93% of theory) with a melting point of 133°–135° C. (with decomposition).

B: In an analogous manner to Example 1B, the product from step A is reacted with half-concentrated hydrochloric acid to give 7-(1-aminomethyl-2-oxa-7-aza-bicyclo[3.3.0] oct-7-yl)-6-fluoro-1-(cis-2-fluorocyclopropyl)-1,4-dihydro-4-oxo-3-quinolinecarboxylic acid hydrochloride with a melting point of 180°–185° C. (with decomposition).

EXAMPLE 10

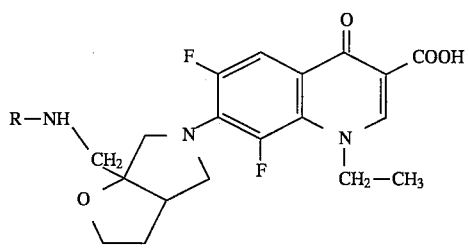

A: R = (CH$_3$)$_3$C—O—CO

B: R = H × HCl

A: In an analogous manner to Example 1A, reaction is effected with 1-ethyl-6,7,8-trifluoro-1,4-dihydro-4-oxo-3-quinolinecarboxylic acid to give 7-(1-tert-butoxycarbonylaminomethyl-2-oxa-7-azabicyclo[3.3.0]oct-7-yl)-1-ethyl-6,8-difluoro-1,4-dihydro-4-oxo-3-quinolinecarboxylic acid (83% of theory) with a melting point of 234°–236° C. (with decomposition).

B: In an analogous manner to Example 1B, the product from step A is reacted with half-concentrated hydrochloric acid to give 7-(1-aminomethyl-2-oxa-7-azabicyclo[3.3.0] oct-7-yl)-1-ethyl-6,8-difluoro-1,4-dihydro-4-oxo-3-quinolinecarboxylic acid hydrochloride with a melting point of 218°–223° C. (with decomposition).

EXAMPLE 11

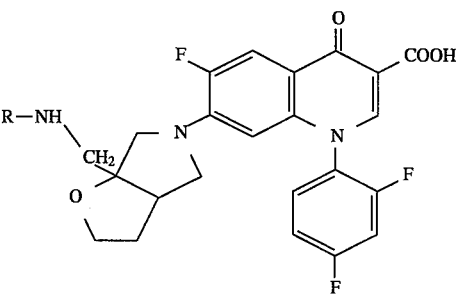

A: R = (CH$_3$)$_3$C—O—CO

B: R = H × HCl

A: In an analogous manner to Example 1A, reaction is effected with 1-(2,4-difluoro-phenyl)-6,7-difluoro-1,4-dihydro-4-oxo-3-quinolinecarboxylic acid to give 7-(1-tert-butoxycarbonylaminomethyl-2-oxa-7-azabicyclo[3.3.0]oct-7-yl)-1-(2,4-difluorophenyl)-6-fluoro-1,4-dihydro-4-oxo-3-quinolinecarboxylic acid (93% of theory) with a melting point of 125°–130° C. (with decomposition).

B: In an analogous manner to Example 1B, the product from step A is reacted with half-concentrated hydrochloric acid to give 7-(1-aminomethyl-2-oxa-7-azabicyclo[3.3.0]oct-7-yl)-1-(2,4-difluorophenyl)-6-fluoro-1,4-dihydro-4-oxo-3-quinolinecarboxylic acid hydrochloride with a melting point of 235° C. (with decomposition).

EXAMPLE 12

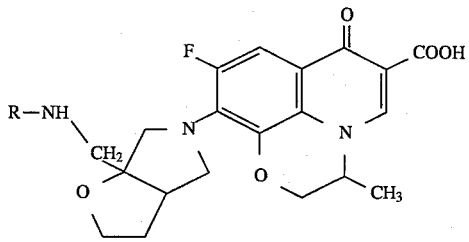

A: R = (CH$_3$)$_3$C—O—CO

B: R = H × HCl

A: In an analogous manner to Example 1A, reaction is effected with 9,10-difluoro-3-methyl-7-oxo-2,3-dihydro-7H-pyrido[1,2,3-de][1,4]benzoxazine-6-carboxylic acid to give 10-(1-tert-butoxycarbonylaminomethyl-2-oxa-7-azabicyclo[3.3.0]oct-7-yl)-9-fluoro-3-methyl-7-oxo-2,3-dihydro-7H-pyrido[1,2,3-de][1,4]benzoxazine-6-carboxylic acid (21% of theory) with a melting point of 176°–179° C. (with decomposition).

B: In an analogous manner to Example 1B, the product from step A is reacted with half-concentrated hydrochloric acid to give 10-(1-aminomethyl-2-oxa-7-aza-bicyclo[3.3.0]oct-7-yl)-9-fluoro-3-methyl-7-oxo-2,3-dihydro-7H-pyrido[1,2,3-de][1,4]benzoxazine-6-carboxylic acid hydrochloride with a melting point of 220°–227° C. (with decomposition).

EXAMPLE 13

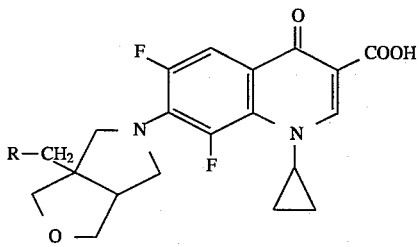

A: R = 3-NO$_2$—C$_6$H$_4$—CH=N—

B: R = HCl × NH$_2$—

A: 581 mg (4.1 mmol) of 1-aminomethyl-3-oxa-7-azabicyclo[3.3.0]octane are dissolved in 5 ml of acetonitrile, and a solution of 650 mg (4.3 mmol) of 3-nitrobenzaldehyde in 5 ml of acetonitrile is added. The mixture is left to stand at room temperature for 1 hour, and is then diluted with 3 ml of dimethylformamide; 672 mg (6 mmol) of 1,4-diazabicyclo[2.2.2]octane and 850 mg (3 mmol) of 1-cyclopropyl-6,7,8-trifluoro-1,4-dihydro-4-oxo-3-quinolinecarboxylic acid are then added and the mixture is heated under reflux for 3 hours. The precipitate is filtered off with suction, washed with acetonitrile and water, and dried at 100° C. in an air-circulating drying oven. Yield: 948 mg (60% of theory) of 1-cyclopropyl-6,8-difluoro-1,4-dihydro-7-(3-nitrobenzylideneamino-methyl-3-oxa-7-azabicyclo[3.3.0]oct-7-yl)-4-oxo-3-quinolinecarboxylic acid, Melting point: 220°–230° C. (with decomposition) (recrystallised from dimethylformamide).

B: 526 mg (1 mmol) of the product from step A are dissolved in 12 ml of 5N hydrochloric acid. The mixture is extracted with dichloromethane, and the aqueous phase is separated off, washed with dichloromethane and evaporated; the residue is then stirred with ethanol and the resulting salt is filtered off with suction, washed with ethanol, and dried at 100°–120° C. under high vacuum.

Yield: 370 mg (84% of theory) of 7-(1-aminomethyl-3-oxa-7-azabicyclo[3.3.0]oct-7-yl)-1-cyclopropyl-6,8-difluoro-1,4-dihydro-4-oxo-3-quinolinecarboxylic acid hydrochloride, Melting point: 245°–249° C. (with decomposition).

EXAMPLE 14

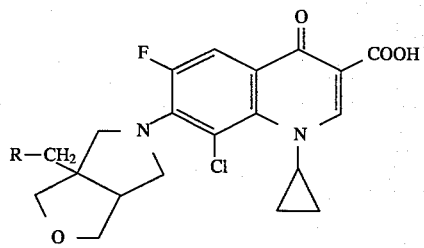

A: R = 3-NO$_2$—C$_6$H$_4$—CH=N—

B: R = HCl × NH$_2$—

A: In an analogous manner to Example 13, reaction is effected with 8-chloro-1-cyclopropyl-6,7-difluoro-1,4-dihydro-4-oxo-3-quinolinecarboxylic acid to give 8-chloro-1-cyclopropyl-6-fluoro-1,4-dihydro-7-(3-nitro-benzylideneaminomethyl)-3-oxa-7-azabicyclo[3.3.0]oct-7-yl)-4-oxo-3-quinolinecarboxylic acid. Melting point: 222°–224° C. (with decomposition).

B: 910 mg (1.7 mmol) of the product from Example 14 in 64 ml of dichloromethane are treated with 22 ml of 3N hydrochloric acid for 30 minutes in an ultrasonic bath. The aqueous phase is separated off, extracted again with dichloromethane, and concentrated, and the residue is stirred with ethanol. The precipitate is filtered off with suction and dried at 90° C. under high vacuum. Yield: 700 mg (91% of theory) of 7-(1-aminomethyl-3-oxa-7-azabicyclo[3.3.0]oct-7-yl)-8-chloro-1-cyclopropyl-6-fluoro-1,4-dihydro-4-oxo-3-quinolinecarboxylic acid hydrochloride, Melting point: sinters from 168° C., at 188° C. decomposition with foaming.

We claim:

1. A process for the preparation of a compound of the formula

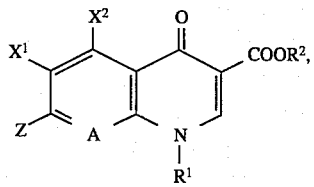

in which

X$^1$ represents halogen or nitro,

X$^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl, R¹ represents alkyl having 1 to 4 carbon atoms, alkenyl having 2 to 4 carbon atoms, cycloalkyl having 3 to 6 carbon atoms, which is optionally substituted by halogen, bicyclo[1.1.1]pent-1-yl, 1,1-dimethylpropargyl, 3-oxetanyl, 2-hydroxyethyl, 2-fluoroethyl, methoxy, amino, methylamino, ethylamino, dimethylamino, or phenyl which is optionally substituted by 1 or 2 fluorine atoms, R² represents hydrogen, alkyl having 1 to 4 carbon atoms, which is optionally substituted by hydroxyl, methoxy, amino, methylamino or dimethylamino, or (5-methyl-2-oxo-1,3-diaxol-4-yl)-methyl, Z represents a residue of the structure

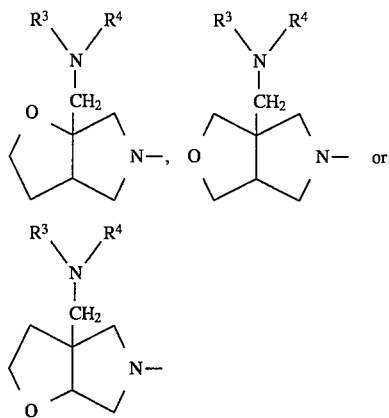

in which
R³ represents hydrogen, methyl or ethyl,
R⁴ represents hydrogen, acyl having 1 to 3 carbon atoms, alkoxycarbonyl having 1 to 4 carbon atoms in the alkyl moiety, or methyl, and
A represents N or C—R⁵, in which
R⁵ represents hydrogen, halogen, methyl, alkenyl having 2 to 3 carbon atoms, alkinyl having 2 to 3 carbon atoms, hydroxyl or methoxy, or, together with R¹, can form a bridge of the structure

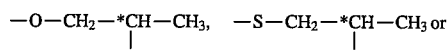

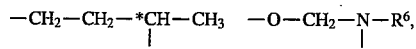

in which R⁶ denotes hydrogen, methyl or formyl,
which comprises reacting a compound of the formula

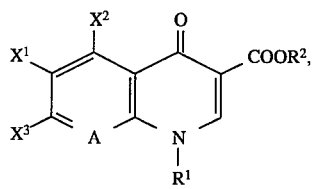

in which
X³ represents halogen, with a compound of the formula

Z'—H    (III)

in which
Z' has the meaning given above for Z or represents a residue Z whose amino group is blocked by a protective group, optionally in the presence of an acid-capturing agent, and optionally eliminating any protective group which may be present.

2. A process according to claim 1, in which
X¹ represents fluorine,
X² represents hydrogen, amino, methylamino, hydroxyl, methoxy, fluorine, chlorine, bromine or methyl,
R¹ represents alkyl having 1 to 3 carbon atoms, vinyl, cycloalkyl having 3 to 4 carbon atoms, 2-(cis- or trans-)fluorocyclopropyl, or phenyl which is optionally substituted by 1 or 2 fluorine atoms,
R² represents hydrogen, alkyl having 1 to 2 carbon atoms, which is optionally substituted by amino, methylamine or dimethylamino, or (5-methyl-2-oxo-1,3-dioxol-4-yl)-methyl,
R⁴ represents hydrogen, acyl having 1 to 2 carbon atoms, alkoxycarbonyl having 1 to 4 carbon atoms in the alkyl moiety, or methyl, and
R⁵ represents hydrogen, fluorine, chlorine, methyl, vinyl, ethinyl, or methoxy, or, together with R¹, can form a bridge of the structure

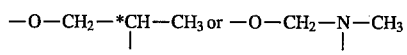

3. A process according to claim 1, in which
X¹ represents fluorine,
X² represents hydrogen, amino or fluorine,
R¹ represents alkyl having 1 to 2 carbon atoms, cyclopropyl, 2-(cis- or trans-)fluorocyclopropyl, or phenyl which is optionally substituted by 1 or 2 fluorine atoms,
R² represents hydrogen or alkyl having 1 to 2 carbon atoms,
R³ represents hydrogen,
R⁴ represents hydrogen or alkoxycarbonyl having 1 to 4 carbon atoms in the alkyl moiety and
R⁵ represents hydrogen, fluorine, chlorine or methoxy, or, together with R¹, can form a bridge of the structure

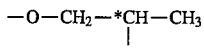

* * * * *

UNITED STATES PATENT AND TRADEMARK OFFICE
CERTIFICATE OF CORRECTION

PATENT NO. : 5,621,105
DATED : April 15, 1997
INVENTOR(S) : Petersen, et al.

It is certified that error appears in the above-indentified patent and that said Letters Patent is hereby corrected as shown below:

Col. 31, line 12    Delete " 3-diaxol-4-yl " and substitute -- 3-dioxol-4-yl --

Col. 32, line 24    Delete " methylamine " and substitute -- methylamino --

Signed and Sealed this

Fifteenth Day of July, 1997

Attest:

BRUCE LEHMAN

*Attesting Officer*          *Commissioner of Patents and Trademarks*